United States Patent
Vaughey et al.

(10) Patent No.: US 10,593,996 B2
(45) Date of Patent: Mar. 17, 2020

(54) HALOGEN-FREE ELECTROLYTES FOR MAGNESIUM BATTERIES

(71) Applicant: UChicago Argonne, LLC, Chicago, IL (US)

(72) Inventors: John T. Vaughey, Elmhurst, IL (US); Niya Sa, Darien, IL (US); Hao Wang, Lemont, IL (US); Baris Key, Lemont, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 79 days.

(21) Appl. No.: 15/685,234

(22) Filed: Aug. 24, 2017

(65) Prior Publication Data

US 2019/0067743 A1    Feb. 28, 2019

(51) Int. Cl.

| | |
|---|---|
| *H01M 10/0569* | (2010.01) |
| *H01M 10/0568* | (2010.01) |
| *H01M 10/0567* | (2010.01) |
| *H01M 10/054* | (2010.01) |
| *C01F 5/00* | (2006.01) |
| *C07C 211/00* | (2006.01) |

(52) U.S. Cl.
CPC .......... *H01M 10/0569* (2013.01); *C01F 5/00* (2013.01); *C07C 211/00* (2013.01); *H01M 10/054* (2013.01); *H01M 10/0567* (2013.01); *H01M 10/0568* (2013.01); *H01M 2300/0025* (2013.01); *H01M 2300/0028* (2013.01)

(58) Field of Classification Search
None
See application file for complete search history.

(56) References Cited

U.S. PATENT DOCUMENTS

| | | |
|---|---|---|
| 2015/0325881 A1 | 11/2015 | Mohtadi |
| 2016/0308203 A1 | 10/2016 | Poeppelmeier et al. |
| 2016/0308248 A1 | 10/2016 | Burrell et al. |

FOREIGN PATENT DOCUMENTS

| | | | |
|---|---|---|---|
| WO | WO 2009/015253 | * | 1/2009 |
| WO | WO-2013/122783 A1 | | 8/2013 |

OTHER PUBLICATIONS

Mohtadi et al., "Magnesium batteries: Current state of the art, issues and future perspectives," Beilstein J. of Nanotechnol. (2014) 5, 1291-1311.
Muldoon et al., "Electrolyte roadblocks to a magnesium rechargeable battery," Energy & Environmental Science (2012), 5, 5941-5950.
Sa et al., "Is alpha-$V_2O_5$ a cathode material for Mg insertion batteries?" J Power Sources (2016), 323, 44-50.
Sa et al., "Role of Chloride for a Simple, Non-Grignard Mg Electrolyte in Ether Based Solvents," ACS Appl Mater Interfaces (2016) (7 pages).
Yagi et al., "Electrochemical Stability of Magnesium Battery Current Collectors in a Grignard Reagent-Based Electrolyte," J Electrochem Soc (2013), 160, C83-C88.

* cited by examiner

*Primary Examiner* — Sarah A. Slifka
(74) *Attorney, Agent, or Firm* — Foley & Lardner LLP

(57) ABSTRACT

An electrochemical cell includes a high voltage cathode configured to operate at 1.5 volts or greater, an anode including $Mg^0$, and an electrolyte including an at least one organic solvent, at least one magnesium salt, and at least one additive agent including a Lewis base, wherein the electrolyte is halogen-free.

25 Claims, 5 Drawing Sheets

FIG. 2A
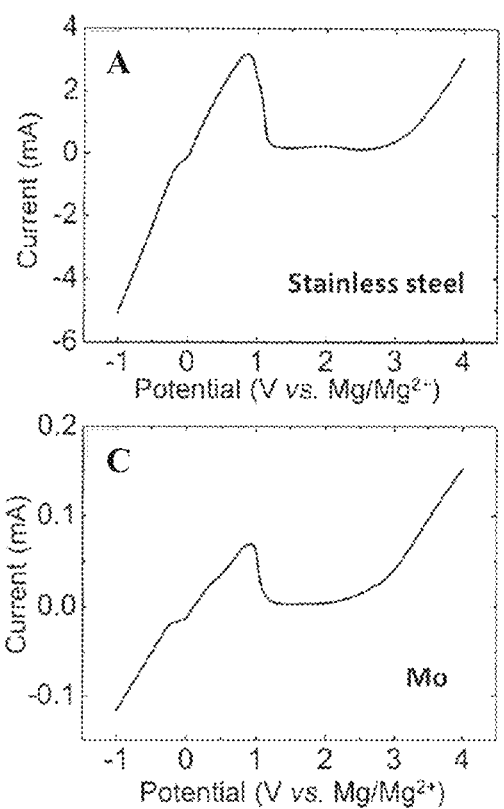
FIG. 2B
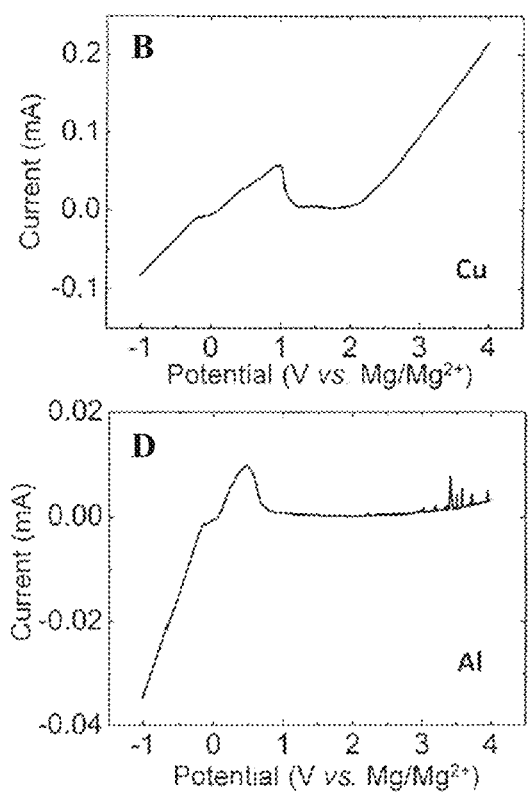
FIG. 2C
FIG. 2D

FIG. 5A
FIG. 5B
FIG. 5C
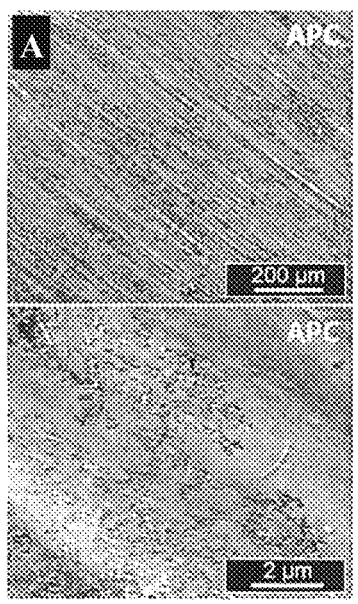
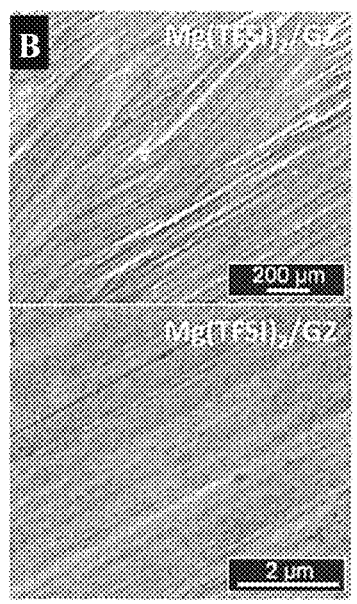
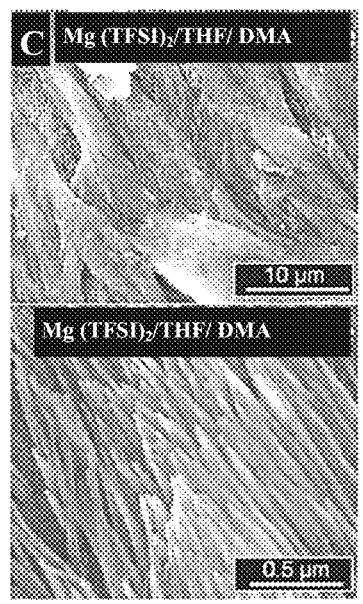

US 10,593,996 B2

HALOGEN-FREE ELECTROLYTES FOR MAGNESIUM BATTERIES

GOVERNMENT RIGHTS

The United States Government has rights in this invention pursuant to Contract No. DE-AC02-06CH11357 between the U.S. Department of Energy and UChicago Argonne, LLC, representing Argonne National Laboratory.

FIELD

The present technology is generally related to magnesium batteries. In particular, the technology is related to electrolytes for magnesium batteries.

BACKGROUND

Electricity generated from clean and renewable sources, such as water, wind, or sunlight, can be successfully converted to electrical energy if the generated electrical energy can be storage efficiently stored and distributed by high capacity secondary batteries. In this regard, rechargeable ion batteries have attracted global attention in the expansion of clean and renewable energy research. Multivalent ion batteries are being increasingly explored as an alternative to lithium-ion batteries (LIBs) which can be damaged owing to their tendency to form dendrites at the anode at a high rate. Given the potential of multivalent ions to yield more than one electron transfer for each redox reaction, their use is likely to result in batteries having high capacity and fast charge ability for energy storage. However, multivalent ions, such as $Ni^{2+}$, $Zn^{2+}$, $Mg^{2+}$, $Ca^{2+}$, $Ba^{2+}$ ions, which have been explored for battery systems that operate with divalent charge, come with their own set of challenges, such as formulating an electrolyte capable of reversible plating, low operating voltage, and lack of cathode compatibility.

Electrolyte development is one of the major challenges in the development of a secondary Mg ion battery design. Halogen containing magnesium electrolytes, such as Grignard reagents (R—Mg—X, where R is an organic residue and X is halogen), have achieved reversible Mg deposition and dissolution, however, their widespread use is impaired by the corrosive nature of the halogen, and the corrosive nature can cause damage to the electrolyte cell components, such as the current collectors. Additionally, halogen containing electrolytes are not known to be compatible with cathodes other than low voltage Chevrel-type cathodes.

Electrolytes based upon magnesium bis(trifluoromethylsulfonylimide) ("$Mg(TFSI)_2$") have also drawn considerable interest not only due to its simplicity, but also its anodic stability from the conjugated TFSI anion structure, yet there are a number of challenges associated with its use. For example, electrolytes containing a tetrahydrofuran (THF) solution of magnesium bis (trifluoromethylsulfonylimide) and magnesium chloride ($Mg(TFSI)_2/MgCl_2$) require a strong Lewis acid such as $AlCl_3$. However, the $AlCl_3$ reacts toward THF, and the generated TFSI anions can potentially lead to the decomposition of the magnesium anode surface. $Mg^{+2}$ in glymes have proven to intercalate with oxides cathode, namely $V_2O_5$, $V_2O_5.xH_2O$, although these systems do not exhibit sufficient columbic efficiency to be found acceptable for large scale applications.

Synthetic strategies to develop Mg electrolytes which can achieve improved reversible Mg deposition while overcoming concerns related to corrosion and limited cathode compatibility are, therefore, needed.

SUMMARY

In one aspect, an electrolyte is provided including at least one organic solvent, at least one magnesium salt, and at least one additive agent including a Lewis base, wherein the electrolyte is halogen-free.

In another aspect, an electrochemical cell is provided including a cathode, an anode which includes magnesium metal, and an electrolyte which includes at least one organic solvent, at least one magnesium salt, and at least one additive agent comprising a Lewis base, wherein the electrolyte is halogen-free. In the electrode, the cathode may include $TiO_2$, $MnO_2$, $Y_2O_3$, $MgCo_2O_4$, $MgCr_2O_4$, $Mg(CrTi)_2O_4$, $VOPO_4$, $MoO_3$, $Mg(VO_3)_2$, Chevrel phase $Mo_6S_8$, and the like, or a mixture of any two or more thereof.

In any of the above embodiments, the Lewis base includes dialkylamine, trialkytlamine, dialkylphosphine, trialkylphosphine, pyridine, a polymeric amine, or a mixture of any two or more thereof. In some embodiments, the Lewis base is selected from the group consisting of dimethylamine, trimethylamine, diethylamine, triethylamine, diisopropylamine, triisopropylamine, triphenylamine, diphenylamine, or a mixture of any two or more thereof. In some embodiments, the additive agent includes dimethylamine. In any of the above embodiments, the additive agent may be present in the electrolyte at a concentration in the range of about 0.1 M to about 1.5 M.

In any of the above embodiments, the magnesium salt includes $(Mg(TFSI)_2$, $Mg[B(C_2O_4)_2]_2$, $Mg[BF_2(C_2O_4)]_2$, $Mg(ClO_4)_2$, $Mg(BF_4)_2$, $Mg(PF_6)_2$, $Mg(AsF_6)_2$, $Mg(SbF_6)_2$, $MgBr_2$, $Mg(CF_3SO_3)_2$, $Mg(CF_3SO_2)_2$, $Mg(C(CF_3SO_2)_3)_2$, $Mg(B(C_6F_5)_4)_2$, $Mg(B(C_6H_5)_4)_2$, $Mg(N(SO_2CF_3)_2)_2$, $Mg(N(SO_2CF_2CF_3)_2)_2$, $Mg(N(SO_2C_2F_5)_2)_2$, $Mg(BF_3C_2F_5)_2$, $Mg(PF_3(CF_2CF_3)_3)_2$, or a mixture of any two or more thereof. In some embodiments, the magnesium salt includes $(Mg(TFSI)_2$.

In any of the above embodiments, the organic solvent may be an aprotic solvent. In any of the above embodiments, the aprotic solvent may include tetrahydrofuran, 2-methyl tetrahydrofuran, dimethoxyethane, diethoxyethane, glyme, monoglyme, dimethyl glycol, ethylene glycol dimethyl ether, diethyl ether, ethyl glyme, diglyme(G2), proglyme, ethyl diglyme, triglyme, butyl diglyme, tetraglyme, polyglyme, or higlyme, hexane, toluene, dimethylsulfoxide, acetonitrile, ionic liquids, or a mixture of any two or more thereof. In some embodiments, the organic solvent includes diglyme. In other embodiments, the organic solvent includes tetrahydrofuran.

In any of the above embodiments, the magnesium salt includes $(Mg(TFSI)_2$ or $(Mg(FSI)_2$, the solvent includes diglyme or tetrahydrofuran, and the additive agent includes dimethylamine.

BRIEF DESCRIPTION OF THE DRAWINGS

FIGS. 2A-2D are graphs illustrating electrochemical stability evaluation of the $Mg(TFSI)_2$/THF/dimethylamine electrolyte on different current collectors: (A) stainless steel current collector, (B) Cu current collector, (C) Mo current collector, and (D) Al current collector, according to the examples.

FIGS. 5A-5C illustrate confirmation of reversible Mg deposition: (A) SEM images of Mg deposition from APC electrolyte, (B) SEM of deposited Mg from Mg(TFSI)$_2$/G2 electrolyte, and (C) SEM of deposited Mg from the dimethylamine-additive (D-additive) electrolyte, according to the examples.

DETAILED DESCRIPTION

Figure 1:
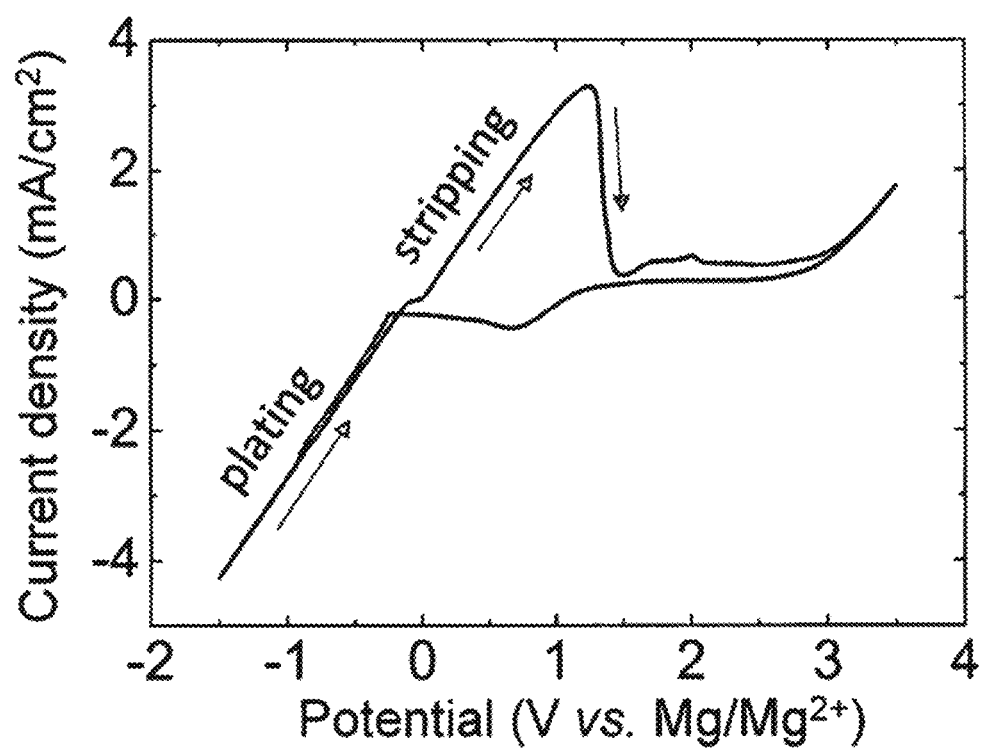
FIG. 1 illustrates the reversible deposition of magnesium for an 0.5 M $Mg(TFSI)_2$/THF/dimethylamine electrolyte at a concentration, with a platinum disk as the working electrode, and magnesium metal as the reference and counter electrode for cyclic voltammetry (CV) and linear sweep voltammetry (LSV), at a scan rate of 25 mV/sec, according to the examples.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The lack of electrolytes that can plate/strip magnesium, and at the same time be compatible with high voltage cathode materials, such as oxide cathodes, is a major roadblock in the development of magnesium batteries. The majority of magnesium electrolytes reported in the literature contain halogen as a component. Although increasing the halogen contents in electrolytes is reported to potentially improve the plating/stripping efficiency of Mg, and reduce the over-potential on the Chevrel phase cathodes, factors such as the corrosive nature of halogen-containing electrolytes and their limited compatibility cathodes other than Chevrel phase cathodes, have hampered their development.

A major limiting component of multi-valent batteries is the transport of larger ions and the degradation of electrolyte with oxides, and therefore improvements in the electrolyte performance are necessary.

Disclosed herein are a halogen-free electrolytes for magnesium batteries. The halogen-free electrolytes avoid the use of a Grignard Reagents with or without the use of AlCl$_3$ and MgCl$_2$, by providing a magnesium electrolyte, that can reversibly deposit magnesium, and which is compatible with a number of oxide cathode materials for multivalent ion batteries. The electrolyte shows reversible magnesium deposition and dissolution without the use of Grignard reagents, organometallic materials, Lewis acids or related anions. Anode performance of the electrolyte is comparable with a classical halogen-containing electrolytes, for example, PhMgCl—AlCl$_3$/THF-based (APC), however with a less corrosive nature. Concurrently, over-potential of the electrolyte of the present technology is less than that of the classical, conventional, non-halogen-containing electrolytes. The halogen-free electrolytes have higher stability with varying cathodes as well as multiple current collectors as compared to convention Mg batteries. Additionally, these electrolyte systems are not restricted to magnesium ion batteries, which are described herein as an illustrative embodiment, but have potential application in lithium air batteries as well as other multivalent ion batteries based on metals including, but not limited to, calcium, strontium, barium, zinc, scandium, and yttrium.

In one aspect, an electrolyte is provided for a high voltage magnesium ion battery, the battery including a magnesium metal anode. The electrolyte is halogen-free and provides for reversible deposition of magnesium, and is compatible with high voltage cathode active materials. The electrolyte includes an organic solvent, a magnesium salt, and an additive agent. In such embodiments, the organic solvent may be any solvent that is suitable for ion conduction and is substantially non-reactive with the other components of the electrolyte, or with the components present in an electrochemical cell containing the electrolyte, under operating conditions. Illustrative solvents include, but are not limited to, an ether, a sulfoxide, a nitrile, a hydrocarbon, an aromatic, a carbonate, an amine, or a mixture of any two or more such solvents. In some embodiments, the organic solvent may be an aprotic solvent. Illustrative aprotic solvents include, but are not limited to, ethers, organic carbonates, lactones, ketones, nitriles, ionic liquids, aliphatic, aromatic hydrocarbon solvents, organic nitro solvents, or a mixture of any two or more thereof. Suitable aprotic solvents include, but are not limited to, tetrahydrofuran, 2-methyl tetrahydrofuran, dimethoxyethane, diethoxyethane, glyme, monoglyme, dimethyl glycol, ethylene glycol dimethyl ether, diethyl ether, ethyl glyme, diglyme, proglyme, ethyl diglyme, triglyme, butyl diglyme, tetraglyme, polyglyme, or higlyme, hexane, toluene, dimethylsulfoxide, acetonitrile, ionic liquids, and mixtures of any two or more thereof. In some embodiments, the organic solvent is diglyme. In other embodiments, the organic solvent is tetrahydrofuran (THF).

The amount of solvent in the electrolyte may be such that it is sufficient to at least partially dissolve the conductive magnesium salt. In some embodiments, the amount of the solvent in the electrolyte may be from about 1 wt. % to about 90 wt. %. This includes from about 1 wt. %, to about 90 wt. %, about 5 wt. % to about 80 wt. %, about 10 wt. % to about 70 wt. %, about 15 wt. % to about 60 wt. %, about 20 wt. % to about 50 wt. %, about 30 wt. % to about 40 wt. %, of the total weight of the electrolyte, and ranges between any two of these values or less than any one of these values.

The conductive salts for use in the electrolyte may include any magnesium salts that are stable and soluble in the chosen solvent. Illustrative salts include, but are not limited to, $Mg(TFSI)_2$, $(Mg(FSI)_2$, $Mg[B(C_2O_4)_2]_2$, $Mg[BF_2(C_2O_4)]_2$, $Mg(ClO_4)_2$, $Mg(BF_4)_2$, $Mg(PF_6)_2$, $Mg(AsF_6)_2$, $Mg(SbF_6)_2$, $MgBr_2$, $Mg(CF_3SO_3)_2$, $Mg(CF_3SO_2)_2$, $Mg(C(CF_3SO_2)_3)_2$, $Mg(B(C_6F_5)_4)_2$, $Mg(B(C_6H_5)_4)_2$, $Mg(N(SO_2CF_3)_2)_2$, $Mg(N(SO_2CF_2CF_3)_2)_2$, $Mg(N(SO_2C_2F_5)_2)_2$, $Mg(BF_3C_2F_5)_2$, or $Mg(PF_3(CF_2CF_3)_3)_2$, or a mixture of any two or more thereof. In some embodiments, the magnesium metal salt is a mixture of any two or more such magnesium metal salts. In some embodiments, the conductive salt includes $Mg(TFSI)_2$. In other embodiments, the conductive salt includes $(Mg(FSI)_2$.

The conductive salt, e.g., a magnesium salt, may be present in the electrolytes at a concentration that is sufficient for use in the intended battery applications. In some embodiments, the concentration of the conductive salt in the solvent is from about 0.1 M to about 2.0 M. This includes concentrations from about 0.1 M to about 2.0 M, about 0.5 M to about 1.5 M, about 0.8 M to about 1.2 M, and ranges between any two of these values or less than any one of these values. In some embodiments, the concentration of magnesium salt in the electrolyte is from about 0.1 M to about 1.0 M.

The additive agent of the electrolyte is such that it facilitates the dissolution of the magnesium salt into the aprotic solvent, and which makes reversible Mg deposition possible. Suitable additive agents may include, but are not limited to, dimethylamine $((CH_3)_2NH)$, trimethylamine $((CH_3)_3N)$, diethylamine $((C_2H_5)_2NH)$, triethylamine $((C_2H_5)_3N)$, diisopropylamine $((C_3H_7)_2NH)$, triisopropylamine $((C_3H_7)_3N)$, diphenylamine $((C_6H_5)_2NH)$, triphenylamine $((C_6H_5)_3N)$, magnesium benzoate $(C_{14}H_{10}MgO_4)$, magnesium trifluoromethanesulfonate (Mg $(CF_3SO_3)_2$), magnesium acetylacetonate dehydrate $((CH_3COCHCOCH_3)2Mg.2H_2O)$, $LiBF_4$, or a mixture of any two or more thereof. In some embodiments, the additive agent includes one or more of dimethylamine, diethylamine and $LiBF_4$.

In any of the above embodiments, the additive agent may include a Lewis base. In some embodiments, the Lewis base includes dimethylamine, diethylamine, or a mixture thereof. Illustrative Lewis bases may include, but are not limited to, dialkylamine, trialkytlamine, dialkylphosphine, trialkylphosphine, pyridine, a polymeric amine, or a mixture of any two or more thereof. In some embodiments, the additive agent includes dimethylamine. In other embodiments, the additive agent includes diethylamine. In any of the above embodiments, the additive agent may be a Lewis base which functions as a co-solvent. In some embodiments, the co-solvent is a compound which includes a secondary amine functional group. Suitable co-solvents include secondary amine compounds of formula $(NH)R^1R^2$, wherein $R^1$ and $R^2$ are independently selected from $C_{1-10}$ alkyl group or $C_{3-10}$ cycloalkyl group. In some embodiments, each of $R^1$ and $R^2$ is independently a $C_{1-6}$ alkyl group. Exemplary co-solvent additives include, but are not limited to dimethylamine, diethylamine, methylethylmine, methylpropylamine, ethylpropylamine, diisopropylamine, dibutylamine, diphenylamine, and the like, and combinations thereof. The co-solvent may be added as an aqueous solution of the secondary amine compound.

The amount of co-solvent in the electrolyte may be suitably selected to facilitate the dissolution of the magnesium salt in to the solvent, or solvent and co-solvent mixture. In some embodiments, the amount of the co-solvent in the electrolyte may be from about 1 wt. % to about 90 wt. %. This includes from about 1 wt. %, to about 90 wt. %, about 5 wt. % to about 80 wt. %, about 10 wt. % to about 70 wt. %, about 15 wt. % to about 60 wt. %, about 20 wt. % to about 50 wt. %, about 30 wt. % to about 40 wt. %, of the total weight of the electrolyte, and ranges between any two of these values or less than any one of these values.

The volume ratio of amount of solvent to amount of co-solvent in the electrolyte may suitably range from about 1:2 to about 4:1. In some embodiments, the volume ratio of the solvent to the co-solvent is about 1:2, about 1:1.5, about 1:1, about 1.5:1, about 2:1, about 2.5:1, about 3:1, about 3.5:1, or about 4:1.

The electrolyte composition may be composed of about 10 wt. % to about 90 wt. % of a magnesium salt, about 10 wt. % to about 90 wt. % of an organic co-solvent, about 10 wt. % to about 90 wt. % of an additive. The water content of the electrolyte may vary from about 0.001 wt. % to about 0.00001 wt. %, as determined by Karl-Fischer titration. The electrolyte may have a pH of about 5 to about 8.

The magnesium salt may be soluble in the combination of organic solvent, such as e.g., diglyme or THF, and amine co-solvent, with a solubility of about 0.1 M to about 5.0 M. This includes from about 0.1 M to about 5.0 M, about 0.5 M to about 4.0 M, about 1.0 M to about 3.0 M, about 1.5 M to about 2.5 M, and ranges between any two of these values or less than any one of these values. The electrolyte provides reversible deposition of magnesium, and is also halogen-free, thereby reducing the corrosion possibility. The properties of the electrolyte include high conductivity, high Coulombic efficiency, and an electrochemical window that can exceed 3.5 V vs. $Mg/Mg^{+2}$.

The present electrolytes are compatible with magnesium metal anodes and cathodes beyond the commonly used cathodes. For example, the electrolyte is beneficially compatible with high voltage oxide cathodes including, but not limited to, $TiO_2$, $MnO_2$, $V_2O_5$, $Y_2O_3$, $MgCo_2O_4$, $MgCr_2O_4$, $Mg(CrTi)_2O_4$, $VOPO_4$, $MoO_3$, $Mg(VO_3)_2$, as well as with Chevrel phase $Mo_6S_8$, and the like, or mixtures of any two or more thereof.

In another aspect, an electrochemical cell is provided. The electrochemical cell may include a cathode, an anode, and any of the electrolytes described herein. In one aspect, the electrochemical cell may include rechargeable batteries. Illustrative electrochemical cells include magnesium batteries. The electrochemical cells may also include a separator between the anode and cathode, and the anodes and cathodes may include a current collector and binder.

The electrochemical cells may include cathodes that are based upon high voltage cathode active materials. Illustrative high voltage cathode materials include, but are not limited to, $TiO_2$, $MnO_2$, $V_2O_5$, $V_6O_{13}$, $Y_2O_3$, $MgCo_2O_4$, $MgCr_2O_4$, $Mg(CrTi)_2O_4$, $VOPO_4$, $MoO_3$, $Mg(VO_3)_2$, $Mo_6S_{8-x}Se_x$ ($0 \le x \le 1$), a hydrated vanadium bronze, orthorhombic $MoO_3$, cation deficient spinel $Mn_{2.15}Co_{0.37}O_4$, $MgMnSiO_4$, $MgCoSiO_4$, $MnO_2$, $Mg_{0.5}Ti_2(PO_4)_3$, fluorinated graphite, and the like, or a mixture of any two or more thereof. In some embodiments, the high voltage cathode active materials include, but are not limited to, $MnO_2$, $V_2O_5$, and $V_6O_{13}$. In some embodiments, the cathode includes $V_2O_5$. In some embodiments, the cathode may be a high voltage cathode configured to operate at 1.5 volts or greater.

Anodic materials for use in the electrochemical cell are not particularly limited, but are suitably stable in the solvents and in the presence of the various electrolyte components. Illustrative materials that may be used as the anodic material include, but are not limited to, magnesium, bismuth, $TiO_2$, $TiS_2$, or amorphous carbon. In some embodiments, the anode includes $Mg^0$. Magnesium anodes have low reduction potential, high theoretical volumetric capacity and reduced dendrite formation upon magnesium deposition. Theoretically, magnesium batteries can operate on deposition and dissolution of ions into and out of the metal surface, thereby avoiding issues associated with solid diffusion.

The cathode and/or the anode may include a current collector in communication with the magnesium. Suitable current collectors may be any material that is stable at the voltage of the cell and under the chemical conditions in the cell. Illustrative current collector materials may include, but are not limited to, stainless steel, aluminum, copper, platinum, molybdenum or a carbon-based collector such as graphite.

The cathode and/or the anode may further include a binder to aid in electrical communication of the magnesium with the current collector. Suitable binders include, but are not limited to, poly-vinylidene fluoride (PVdF), poly(vinylidene fluoride-co-hexafluoropropene) (PV dFHFP), polytetrafluoroethylene (PTFE), or a mixture of any two more thereof.

The electrochemical cell may also include a separator which is located between the anode and the cathode, and may prevent direct physical contact between them. The separators may be porous to allow for electron transport between the electrodes, or they may be non-porous. Illustrative separators include, but are not limited to, a paper separator, a polymeric separator, a glass fiber separator, or a ceramic separator, or a combination of any two or more thereof.

In another aspect, a process of preparing a halogen-free electrolyte is provided, the process including adding a conductive magnesium salt to an organic solvent to obtain a solution and mixing the solution to dissolve the magnesium compound, and further adding an additive agent to obtain the electrolyte solution.

In any such embodiments, the conductive magnesium salt, organic solvent, and additive agent as are described herein. In some embodiments, the electrolytes were prepared by dissolving $Mg(TFSI)_2$ in solvents such as, but not limited to, THF, diglyme, triglyme, and/or tetraglyme. When using dimethylamine as an additive agent, which enhances solubility of the $Mg(TFSI)_2$, the solubility in THF is about 2.0 M. In the absence of the additive agent, the solubility of $Mg(TFSI)_2$ in THF is about 0 M. Accordingly, in some embodiments, the additive agent enhances the solubility of the conductive magnesium salt.

The present invention, thus generally described, will be understood more readily by reference to the following examples, which are provided by way of illustration and are not intended to be limiting of the present invention.

EXAMPLES

Example 1

Preparation of Electrolyte: $Mg(TFSI)_2$ in Diglyme. Magnesium bis(trifluoromethane sulfonyl)imide (99.5%, Solvionic, France) was dried in a vacuum oven at 180° C. overnight prior to use. Diglyme (Aldrich, anhydrous, 99.5%) solvent was pretreated with molecular sieves (Aldrich, 3 Å beads, 4-8 mesh) overnight and then added into the dried $Mg(TFSI)_2$. The as-prepared electrolyte was then stirred overnight before use. Water levels of the as prepared electrolytes were determined from Karl-Fischer analysis, and the water content was observed to be less than 15 ppm.

Example 2

Preparation of Electrolyte: $Mg(TFSI)_2$ in THF and dimethylamine. Magnesium bis(trifluoromethane sulfonyl)imide (99.5%, Solvionic, France) was dried in a vacuum oven at 180° C. overnight before use. THF (Aldrich, anhydrous, 99.5%) solvent was pretreated with molecular sieves (Aldrich, 3 Å beads, 4-8 mesh) overnight and then added into the dried $Mg(TFSI)_2$. Dimethylamine was added to the $Mg(TFSI)_2$/THF electrolyte. The as-prepared electrolyte was then stirred overnight before use. Water levels of the as prepared electrolytes were determined from Karl-Fischer analysis, and the water content was observed to be less than 15 ppm. The solubility of $Mg(TFSI)_2$ in THF-DMA is about 2.0 M.

Example 3

Preparation of Electrochemical cell. A coin cell was prepared having a $V_2O_5$ cathode, a 1 M $Mg(TFSI)_2$/THF/dimethylamine electrolyte, and a magnesium metal anode.

Example 4

Electrochemical characterization. Cyclic voltammograms (CV) were obtained using a platinum disk electrode (2 mm in diameter, CH Instruments, Austin, Tex.) as a working electrode, and mechanically polished magnesium ribbons (99.9% purity, Sigma-Aldrich) as the reference and counter electrode. The electrolyte (1 ml) was added to the cell for each CV measurement. Electrochemical Impedance Spectroscopy (EIS) was applied for the electrolyte conductivity measurements. EIS measurements were obtained in a cell having two platinum disks facing each other with 1 mm separation. The conductivity cell was filled with 1 mL electrolyte with the frequency being scanned from 0.1 Hz to 100,000 Hz. Impedance was calculated according to equation (1):

$$k = d/(A \cdot \Xi) \quad (1)$$

where k is ionic conductivity, d is the electrode distance, and A is the area of the electrode. Constants d and A are obtained by calibration of conductivity with a standard solution of 0.1 M, 0.2 M, 0.5 M, 0.7 M, 1.0 M, or 2.0 M potassium chloride. All electrochemical characterizations presented in this work were carried out on a multichannel potentiostat (Parstat MC, Princetion Applied Research, TN) under a pure argon atmosphere in a glove box, where $H_2O$ and $O_2$ levels are kept under 1 ppm.

Electrochemical characterization of the $Mg(TFSI)_2$ in THF-DMA electrolyte illustrates (1) plating and stripping of Mg can be achieved at a wide concentration range, from 0.1 M to 2.0 M, (2) anodic stability is above 3.5 V versus $Mg/Mg^{2+}$ (FIG. 1).

Stability evaluations were conducted for various cathode current collector materials: (a) stainless steel, (b) Cu, (c) Mo, and (d) Al. FIGS. 2A-D show that good stability (>3 V vs $Mg/Mg^{2+}$) was observed for the tested current collectors.

Figure 3:
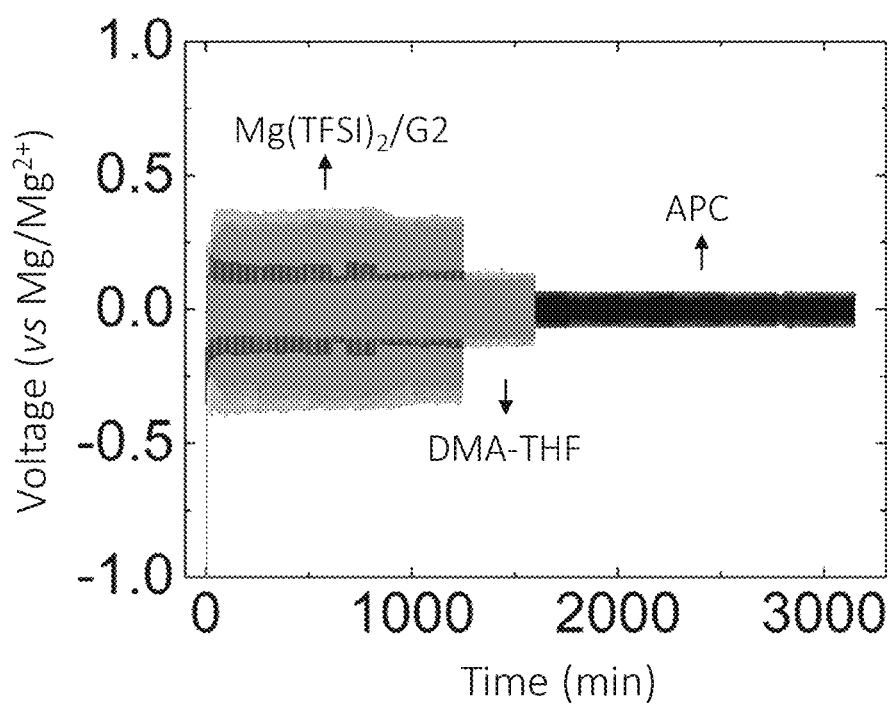
FIG. 3 is a comparison of the cycling performance of a Mg anode versus a Mg symmetric anode for an PhMgCl—AlCl$_3$/THF-based (APC) electrolyte, Mg(TFSI)$_2$/THF electrolyte, and Mg(TFSI)$_2$/THF/dimethylamine electrolyte, according to the examples.

Cyclic voltammetry was conducted on the cells to evaluate the reversibility of Mg deposition from APC, $Mg(TFSI)_2$/diglyme and $Mg(TFSI)_2$/THF/dimethylamine electrolytes at a magnesium anode. FIG. 3 shows that the Mg(TFSI)$_2$/THF/dimethylamine electrolyte system displays higher conductivity than APC and Mg(TFSI)$_2$/diglyme electrolytes.

Figure 4A:
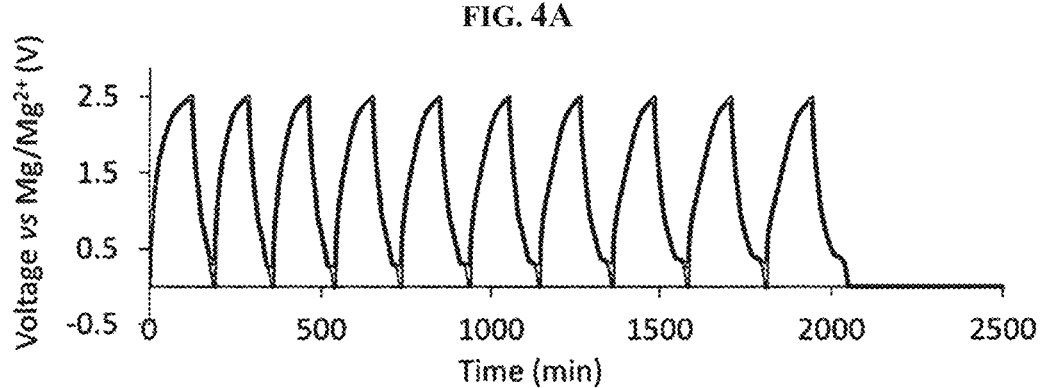
FIGS. 4A and 4B are graphs of coin cell cycling of (A) alpha-MnO$_2$ as cathode and (B) K$_x$TiO$_2$ as cathode, with Mg(TFSI)$_2$/THF/dimethylamine electrolyte, and a Mg metal as anode, with a current density of 20 µA/cm$^2$, according to the examples.
Figure 4B:
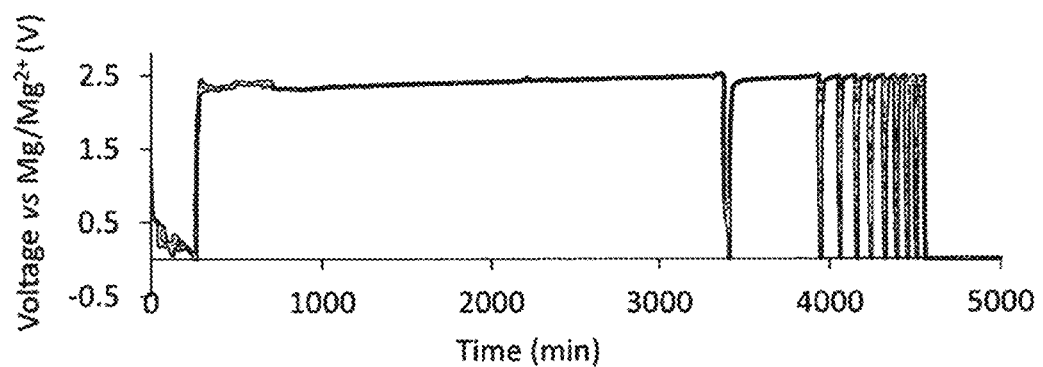

Galvanostatic cycling of the coin cell prepared according to Example 3 demonstrated reversible cycling behavior as shown in FIG. 4. FIGS. 4A and B illustrate the results of additional testing conducted using conventional coin cell having (A) alpha-MnO$_2$ as cathode, and (B) K$_x$TiO$_2$ as cathode. The cells also contain, a Mg(TFSI)$_2$/THF/dimethylamine electrolyte, and magnesium metal as anode, with a current density of 20 µA/cm$^2$. Galvanostatic cycling of the coin cell demonstrated reversible cycling behavior and stability of the cycling for the electrolyte.

Example 5

Scanning Electron Microscopy (SEM). Scanning electron microscopy was performed for the deposited Mg using various electrolytes. Elemental compositions were determined using a standardless ZAF (atomic number, absorption and fluorescence) corrected analysis using atomic number, absorption and fluorescence. SEM was performed at an electron energy of 20 keV. FIGS. 5A, B, and C illustrate the SEM images of Mg deposition from standard APC electrolyte, Mg(TFSI)$_2$/diglyme electrolyte, and Mg(TFSI)$_2$/THF/dimethylamine (D-additive) electrolyte. The SEM images exhibit pure Mg deposition with ordered Mg metal arrays.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An electrolyte comprising:
   at least one organic solvent;
   at least one magnesium salt; and
   at least one additive agent comprising a Lewis base;
   wherein the electrolyte is halogen-free.

2. The electrolyte of claim 1, wherein the Lewis base is a dialkylamine, a trialkytlamine, a dialkylphosphine, a trialkylphosphine, a pyridine, a polymeric amine, or a mixture of any two or more thereof.

3. The electrolyte of claim 2, wherein the Lewis base is dimethylamine, trimethylamine, diethylamine, triethylamine, diisopropylamine, triisopropylamine, triphenylamine, diphenylamine, or a mixture of any two or more thereof.

4. The electrolyte of claim 1, wherein the additive agent comprises dimethylamine.

5. The electrolyte of claim 1, wherein the concentration of the additive agent in the electrolyte is about 10 wt. % to about 90 wt. %.

6. The electrolyte of claim 1, wherein the magnesium salt comprises Mg(TFSI)$_2$, Mg[B(C$_2$O$_4$)$_2$]$_2$, Mg[BF$_2$(C$_2$O$_4$)]$_2$, Mg(ClO$_4$)$_2$, Mg(BF$_4$)$_2$, Mg(PF$_6$)$_2$, Mg(AsF$_6$)$_2$, Mg(SbF$_6$)$_2$, MgBr$_2$, Mg(CF$_3$SO$_3$)$_2$, Mg(CF$_3$SO$_2$)$_2$, Mg(C(CF$_3$SO$_2$)$_3$)$_2$, Mg(B(C$_6$F$_5$)$_4$)$_2$, Mg(B(C$_6$H$_5$)$_4$)$_2$, Mg(N(SO$_2$CF$_3$)$_2$)$_2$, Mg(N(SO$_2$CF$_2$CF$_3$)$_2$)$_2$, Mg(N(SO$_2$C$_2$F$_5$)$_2$)$_2$, Mg(BF$_3$C$_2$F$_5$)$_2$, Mg(PF$_3$(CF$_2$CF$_3$)$_3$)$_2$, or a mixture of any two or more thereof.

7. The electrolyte of claim 1, wherein the magnesium salt comprises Mg(TFSI)$_2$.

8. The electrolyte of claim 1, wherein the organic solvent comprises an aprotic solvent.

9. The electrolyte of claim 8, wherein the aprotic solvent comprises tetrahydrofuran, 2-methyl tetrahydrofuran, dimethoxyethane, diethoxyethane, glyme, monoglyme, dimethyl glycol, ethylene glycol dimethyl ether, diethyl ether, ethyl glyme, diglyme, proglyme, ethyl diglyme, triglyme, butyl diglyme, tetraglyme, polyglyme, higlyme, propylene carbonate, dimethylsulfoxide, acetonitrile, ionic liquids, or a mixture of any two or more thereof.

10. The electrolyte of claim 1, wherein the organic solvent comprises diglyme.

11. The electrolyte of claim 1, wherein the organic solvent comprises tetrahydrofuran.

12. The electrolyte of claim 1, the magnesium salt comprises $Mg(TFSI)_2$, the solvent comprises tetrahydrofuran, and the additive agent comprises dimethylamine.

13. An electrochemical cell comprising:
   a cathode;
   an anode comprising magnesium metal; and
   an electrolyte;
   wherein:
      the electrolyte comprises:
         at least one organic solvent;
         at least one magnesium salt; and
         at least one additive agent comprising a Lewis base;
      wherein the electrolyte is halogen-free.

14. The electrochemical cell of claim 13, wherein the Lewis base comprises dialkylamine, trialkytlamine, dialkylphosphine, trialkylphosphine, pyridine, a polymeric amine, or a mixture of any two or more thereof.

15. The electrochemical cell of claim 14, wherein the Lewis base comprises dimethylamine, trimethylamine, diethylamine, triethylamine, diisopropylamine, triisopropylamine, triphenylamine, diphenylamine, or a mixture of any two or more thereof.

16. The electrochemical cell of claim 13, wherein the additive agent is dimethylamine.

17. The electrochemical cell of claim 13, wherein the additive agent is present in the electrolyte from about 0.1 M to about 2.0 M.

18. The electrochemical cell of claim 13, wherein the magnesium salt comprises $Mg(TFSI)_2$, $Mg[B(C_2O_4)_2]_2$, $Mg[BF_2(C_2O_4)]_2$, $Mg(ClO_4)_2$, $Mg(BF_4)_2$, $Mg(PF_6)_2$, $Mg(AsF_6)_2$, $Mg(SbF_6)_2$, $MgBr_2$, $Mg(CF_3SO_3)_2$, $Mg(CF_3SO_2)_2$, $Mg(C(CF_3SO_2)_3)_2$, $Mg(B(C_6F_5)_4)_2$, $Mg(B(C_6H_5)_4)_2$, $Mg(N(SO_2CF_3)_2)_2$, $Mg(N(SO_2CF_2CF_3)_2)_2$, $Mg(N(SO_2C_2F_5)_2)_2$, $Mg(BF_3C_2F_5)_2$, $Mg(PF_3(CF_2CF_3)_3)_2$, or a mixture of any two or more thereof.

19. The electrochemical cell of claim 13, wherein the magnesium salt comprises $Mg(TFSI)_2$.

20. The electrochemical cell of claim 13, wherein the organic solvent is an aprotic solvent.

21. The electrochemical cell of claim 20, wherein the aprotic solvent comprises tetrahydrofuran, 2-methyl tetrahydrofuran, dimethoxyethane, diethoxyethane, glyme, monoglyme, dimethyl glycol, ethylene glycol dimethyl ether, diethyl ether, ethyl glyme, diglyme, proglyme, ethyl diglyme, triglyme, butyl diglyme, tetraglyme, polyglyme, or higlyme, hexane, toluene, dimethylsulfoxide, acetonitrile, ionic liquids, or a mixture of any two or more thereof.

22. The electrochemical cell of claim 13, wherein the organic solvent comprises diglyme.

23. The electrochemical cell of claim 13, wherein the organic solvent comprises tetrahydrofuran.

24. The electrochemical cell of claim 13, wherein the magnesium salt comprises $Mg(TFSI)_2$, the solvent comprises tetrahydrofuran, and the additive agent comprises dimethylamine.

25. The electrochemical cell of claim 13, wherein the cathode comprises $TiO_2$, $MnO_2$, $Y_2O_3$, $MgCo_2O_4$, $MgCr_2O_4$, $Mg(CrTi)_2O_4$, $VOPO_4$, $MoO_3$, $Mg(VO_3)_2$, Chevrel phase $Mo_6S_8$, or a mixture of any two or more thereof.

* * * * *